United States Patent [19]

Gross

[11] Patent Number: 5,318,557
[45] Date of Patent: Jun. 7, 1994

[54] MEDICATION ADMINISTERING DEVICE

[75] Inventor: Joseph Gross, Moshav Mazor, Israel

[73] Assignee: Elan Medical Technologies Limited, Westmeath, Ireland

[21] Appl. No.: 20,941

[22] Filed: Feb. 22, 1993

Related U.S. Application Data

[63] Continuation-in-part of Ser. No. 933,637, Aug. 24, 1992, abandoned.

[30] Foreign Application Priority Data

Jul. 13, 1992 [IE] Ireland ................................ 922279

[51] Int. Cl.⁵ ........................ A61K 9/22; A61M 37/00
[52] U.S. Cl. ...................... 604/891.1; 604/890.1; 604/141
[58] Field of Search ............... 604/141, 143, 148, 151, 604/890.1, 891.1, 892.1; 222/95, 61, 386.5

[56] References Cited

U.S. PATENT DOCUMENTS

| | | | |
|---|---|---|---|
| 4,304,232 | 12/1981 | Michaels | 604/55 |
| 4,345,603 | 8/1982 | Schulman | 128/419 PT |
| 4,360,019 | 11/1982 | Portner et al. | 604/891.1 |
| 5,135,499 | 8/1992 | Tafani et al. | 604/141 |
| 5,167,625 | 12/1992 | Jacobsen et al. | 604/891.1 |

Primary Examiner—John G. Weiss
Attorney, Agent, or Firm—Benjamin J. Barish

[57] ABSTRACT

A medication administering device includes a housing introducible into a body cavity and of a material insoluble in the body cavity fluids, but formed with an opening covered by a material which is soluble in body cavity fluids. A diaphragm divides the interior of the housing into a medication chamber including the opening, and a control chamber. An electrolytic cell in the control chamber generates a gas when electrical current is passed therethrough to deliver medication from the medication chamber through the opening into the body cavity at a rate controlled by the electrical current.

18 Claims, 5 Drawing Sheets

MEDICATION ADMINISTERING DEVICE

RELATED APPLICATION

The present application is a continuation-in-part of patent application Ser. No. 07/933,637, filed Aug. 24, 1992 now abandoned.

FIELD AND BACKGROUND OF THE INVENTION

The present invention relates to a medication administering device. The invention is particularly useful when embodied in the form of a pill or capsule to be taken orally, and is therefore described below with respect to this application, but it will be appreciated that the invention could be embodied in other types of medication administering devices, such as suppositories to be taken other than orally, or devices to be introduced into a body cavity surgically.

A number of different types of medication administering devices have been developed for administering medication in a controlled manner and/or at a predetermined location, in order to maximize the efficacy of the medication. One type, called a "smart" pill, as briefly described in Popular Science, May 1992, Page 25, includes a capsule which is adapted to be swallowed. The capsule contains a tiny radio transmitter that transmits a continuous signal as it passes through the body to thereby permit its location in the body to be detected. When it reaches a predetermined location, a computer signals the pill to release its payload, by actuating a piston within the capsule to force out medication contained within a chamber in the capsule.

OBJECTS AND BRIEF SUMMARY OF THE INVENTION

A broad object of the present invention is to provide medication administering devices for administering medication in a controlled manner, and/or at a predetermined location, in order to maximize the efficacy of the medication. A more specific object of the invention is to provide other "smart" pill constructions.

According to the present invention, there is provided a medication administering device comprising a housing of a size enabling it to be introduced into a body cavity of a subject, the housing being of a material insoluble in body cavity fluids, but being formed with an opening; and a displaceable member in the interior of the housing and defining first and second expansible-contractible chambers therein. The first chamber includes the above-mentioned opening and is adapted to receive medication to be delivered through the opening when the device is in the body cavity. The device further includes gas generating means for supplying a gas to the second chamber to expand it and thereby to force medication from the first chamber out through the opening into the body cavity.

According to further features in the described preferred embodiments, the displaceable member is a diaphragm; in addition, the opening in the device is initially closed by material which is soluble in the body cavity fluids.

According to yet further features in the described preferred embodiments, the gas generating means includes electrically-controlled means for generating a gas when energized. In the described preferred embodiments, the electrically-controlled means includes an electrolytic cell having an electrolyte generating a gas in accordance with the electrical current passed through the electrolyte.

According to yet further features in some described embodiments, the outer surface of the housing includes spaced, diverse metal elements which are bridged by the fluids in the body cavity to generate an electromotive force for supplying current to the electrically-controlled means within the housing. In other described embodiments, the housing includes a battery for supplying current to the electrically-controlled means.

In one described embodiment, the housing further includes a sensor for sensing a condition in the body cavity and for controlling the electrically-controlled means in response thereto. In other described embodiments, the gas generating means is electrically controlled by a radio frequency signal or by a magnetic switch actuated externally of the subject after the device has been introduced into the body cavity, or by a manual switch when the device is introduced into the body cavity.

According to further features in yet another described environment, the housing includes an outer sheath of a liquid-swellable material which swells when in contact with fluids in the body cavity and disintegrates over a period of time in the body cavity, to thereby control the residence time of the device in the body cavity.

As will be more particularly described below, a medication administering device constructed in accordance with some or all of the foregoing features may be used to administer medication at controlled rates, at predetermined times, and/or at predetermined locations, so as to maximize the efficacy of the medication.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
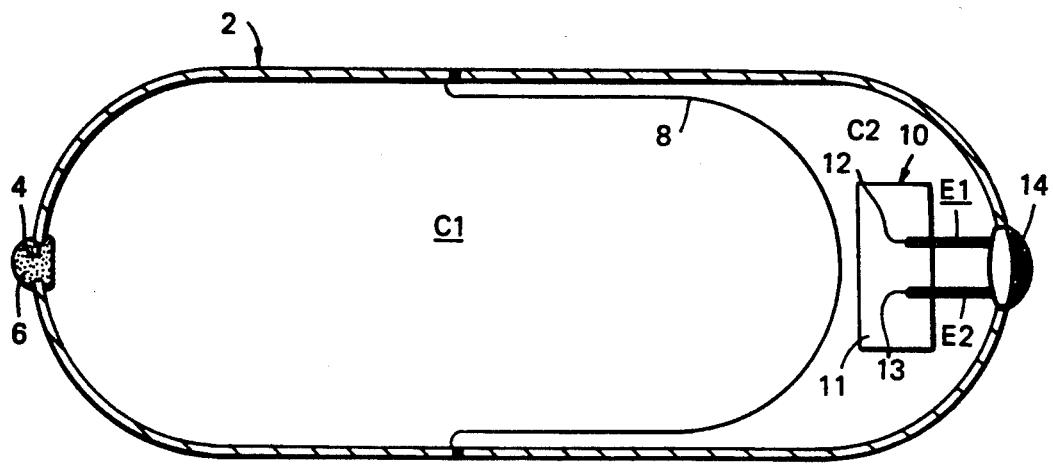
FIG. 1 is a sectional view illustrating one form of device constructed in accordance with the present invention.
Figure 2:
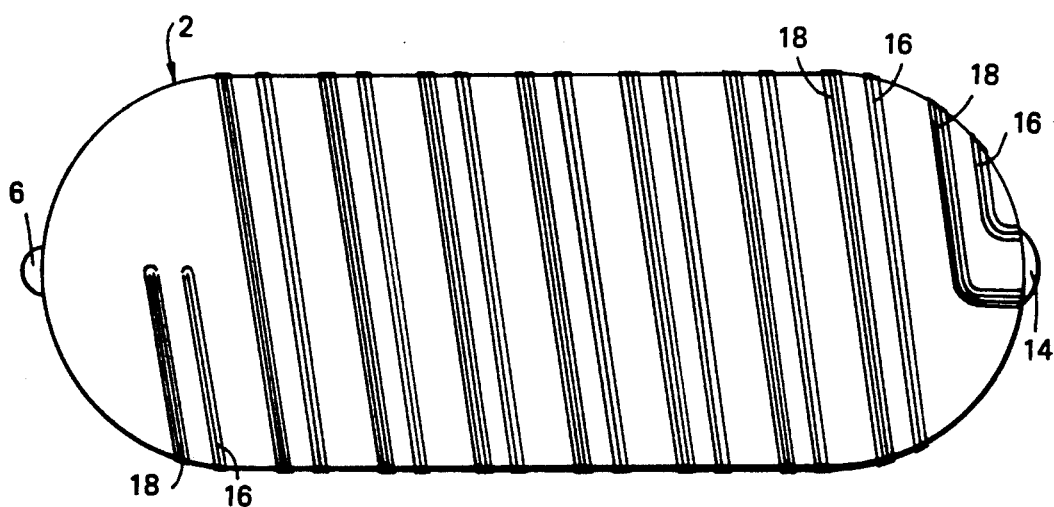
FIG. 2 is a side elevational view of the device of FIG. 1.

The medication administering device illustrated in FIGS. 1 and 2 of the drawings is in the form of a pill or capsule to be taken orally. It includes a housing 2 of a size enabling it to be swallowed by the subject. The housing 2 is of a material which is insoluble in the body cavity (e.g. stomach) fluids, but is formed with an opening 4 covered by a plug 6 which is of a material soluble in the body cavity fluids.

Housing 2 further includes a displaceable member, in the form of a diaphragm 8, dividing the interior of the housing into two expansible-contractible chambers $C_1$, $C_2$. Chamber $C_1$ communicates with housing opening 4 and is adapted to receive the medication to be delivered by the device; and chamber $C_2$ is a control chamber which includes gas generating means for generating a gas to expand chamber $C_2$, and thereby to contract chamber $C_1$ to deliver medication from the latter chamber through opening 4 into the body cavity.

Control chamber $C_2$ thus includes an electrolytic cell generally designated 10, comprising an electrolyte 11 and a pair of electrodes 12, 13 for supplying electrical current to the electrolyte. The electrolyte 11 is of a material which generates a gas according to the amount of electrical current passed through it from the electrodes 12, 13. Preferably, the electrolyte is a solid, e.g., a polymeric gel, and its electrodes are enclosed by a hydrophobic membrane which is permeable by the gas generated in the electrolytic cell, but not permeable by the liquid in the electrolyte. Such electrolytic cells are well known and are described, for example, in our prior U.S. Pat. No. 5,062,834.

The device illustrated in FIGS. 1 and 2 further includes a preprogrammable microprocessor 14 for controlling the rate of application of electrical current to the electrolytic cell 10, and thereby the rate of delivery of medication from chamber $C_1$ via outlet opening 4.

In the embodiment illustrated in FIGS. 1 and 2, the power supplied via the microprocessor 14 to the electrolytic cell 10 is generated in situ by a pair of spaced metal elements 16, 18 wound in the form of strips on the outer surface of the housing 2. The two metal strips 16, 18 are of diverse metal foils (e.g. gold and silver) defining a galvanic cell such that when bridged by the fluids in the body cavity (e.g. stomach acid), they generate an electromotive force for supplying current to the electrolytic cell 10 under the control of the microprocessor 14.

It will be seen that when the device illustrated in FIGS. 1 and 2 is administered orally to a subject, plug 6 dissolves in the stomach fluids, thereby providing communication between the medication chamber $C_1$ and the body cavity. Microprocessor 14, preprogrammed to control the rate of delivery of the medication from chamber $C_1$ to the body cavity, controls the flow of electrical current via electrodes 12, 13 to the electrolyte 11 of the electrolytic cell 10, and thereby controls the rate of generation of the gas within chamber $C_2$. The latter chamber is expanded according to the rate of generation of the gas. As a consequence, chamber $C_1$ is contracted to force medication from chamber $C_1$ via opening 4 to the body cavity according to the rate preprogrammed in microprocessor 14.

Housing 2 may be of any suitable material, such as polyethylene, polycarbonate, etc., which is insoluble in the body cavity fluids and also not deleterious to the body. Plug 6 normally closing opening 4 may be of any suitable material, such as a gelatinous material or other material used in medication capsules, which is soluble in the body cavity fluids, to thereby establish communication between the medication chamber $C_1$ and the body cavity after the device has been swallowed.

In the device of FIGS. 1 and 2, the two metal strips 16, 18 may be helically wound in parallel; however, if a larger voltage is desired than that which can be developed by parallel metal strips, sections of the metal strips can be connected in series to thereby increase the voltage.

Figure 3:
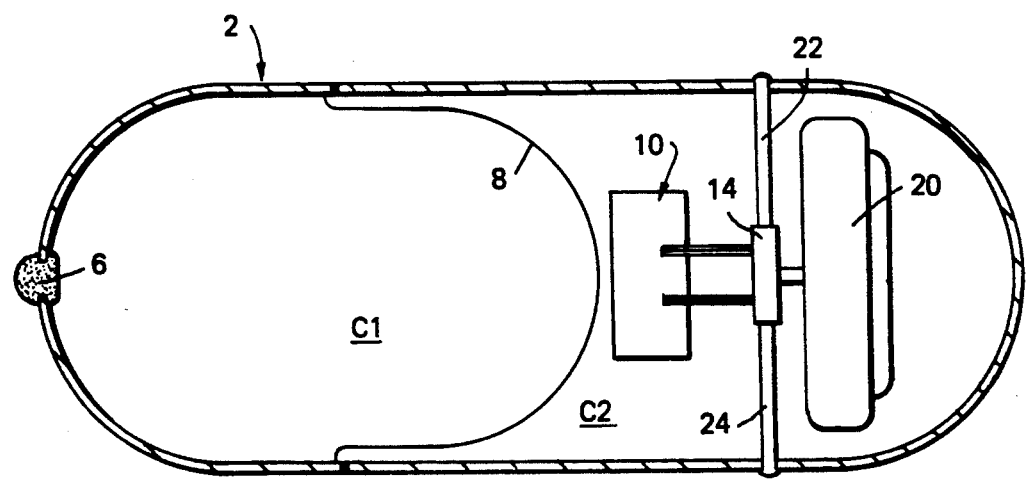
FIGS. 3 and 4 are sectional views illustrating two additional forms of medication administering devices constructed in accordance with the present invention.

FIG. 3 illustrates a device similar to that of FIGS. 1 and 2, with the following exceptions:

First, instead of including the diverse metal strips 16, 18 for generating the electrical power, a battery 20 is included within the device for this purpose.

In addition, the device includes one or more sensors (two being shown at 22, 24) for sensing various conditions within the body and for controlling the microprocessor 14 in response thereto. For example, the sensors may be or include any one or more of the following: (1) a pH sensor, to effect the delivery of the medication (e.g. insulin) only to the small intestine, which has a pH different from that of the stomach, or the delivery of an antacid to the stomach when stomach acidity reaches a certain pH level; (2) a temperature sensor to control the delivery of the medication in response to the body temperature; (3) a sound sensor (e.g. a microphone) to control the delivery of the medication (e.g. nitroglycerine) in response to the pulse rate; or (4) a moisture sensor, to start the delivery of the medication only after the device has been swallowed.

In all other respects, the device illustrated in FIG. 3 is constructed, and operates in the same manner, as the device of FIGS. 1 and 2, and corresponding reference numerals have been applied to its parts in order to facilitate understanding of its construction and operation.

Figure 4:
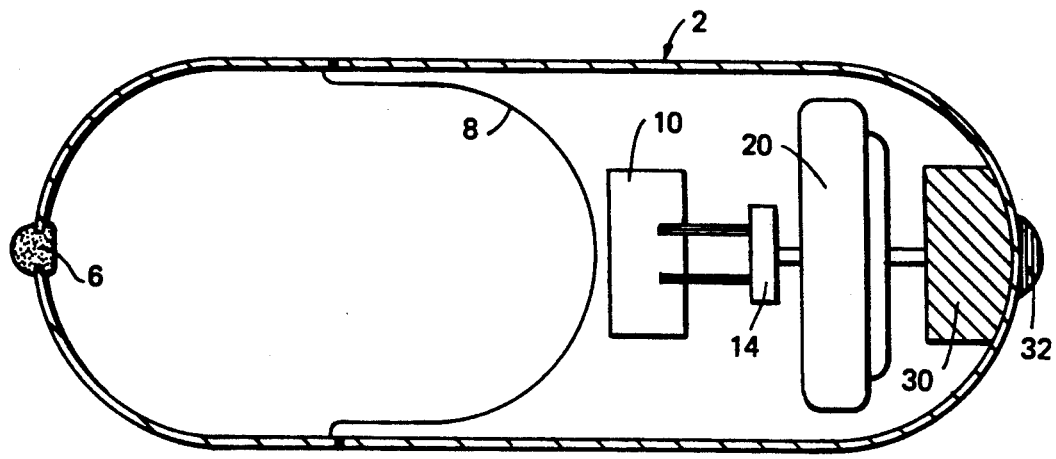
Figure 5:
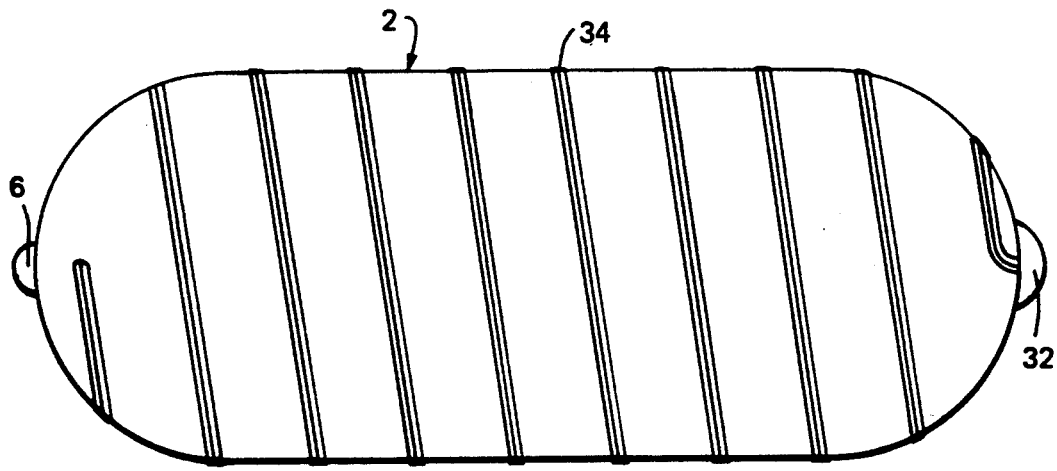
FIG. 5 is a side elevational view illustrating the device of FIG. 4.

FIGS. 4 and 5 illustrate a device similar to that of FIG. 3, and therefore corresponding elements have also been correspondingly numbered. The device of FIGS. 4 and 5, however, includes a control unit 30, e.g., a radio frequency (RF) transmitter/receiver, within housing 2 and connected via a connection 32 to an antenna 34 helically mounted on the outer face of the housing. The device of FIGS. 4 and 5 thus enables the microprocessor 14 within housing 2 to transmit externally its location, and/or to be controlled externally by an RF transmitter (not shown). The external transmitter may thus control the time and/or the rate of application of electrical current to the electrolytic cell 10, and thereby the location and/or rate of delivery of the medication from chamber $C_1$ to the body cavity of the subject.

Instead of being a radio frequency transmitter/receiver, control unit 30 in FIG. 4 could be an electrical switch, such as a reed switch, which can be magnetically actuated by a magnetic field externally of the subject.

Figure 6:
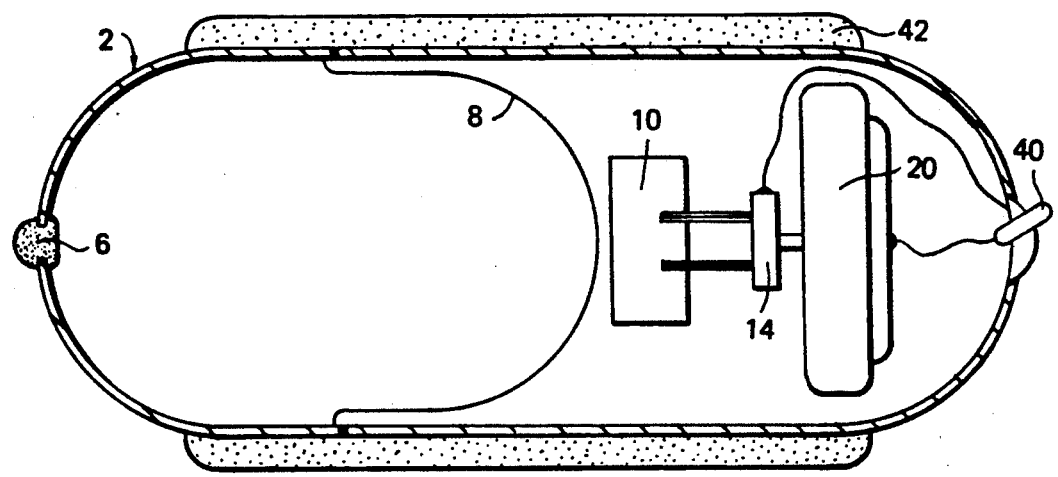
FIG. 6 is a sectional view illustrating a still further form of medication administering device constructed in accordance with the present invention.
Figure 7:
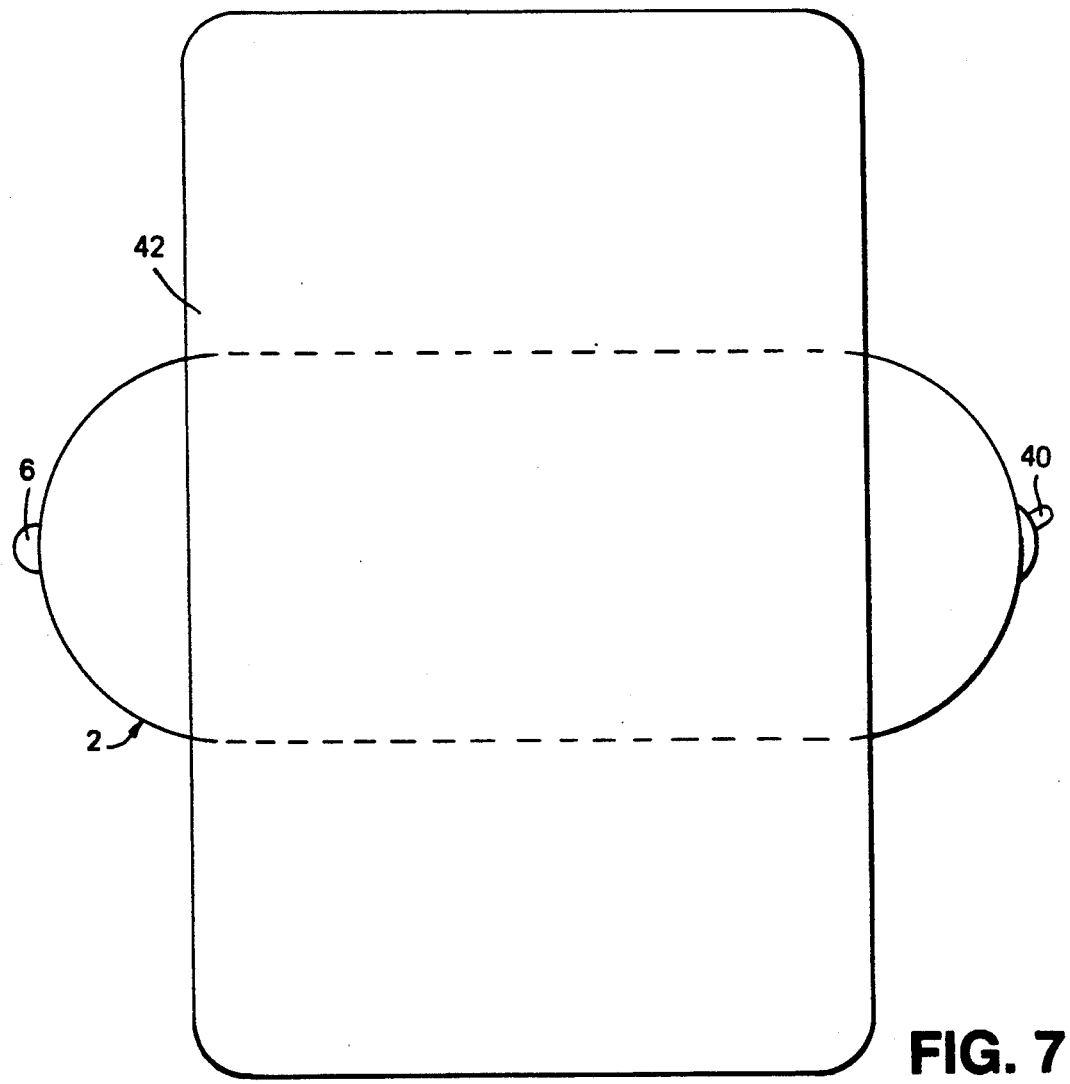
FIG. 7 is a side elevational view illustrating the device of FIG. 6 in its condition within the subject's body cavity.

FIGS. 6 and 7 illustrate a further device similar to that of FIG. 3, and therefore its parts are correspondingly numbered, but with the following differences:

A first difference is that the device includes a mechanical switch 40 which may be mechanically actuated, e.g. just before swallowing the device, to actuate the microprocessor 14 controlling the supply of electrical current to electrolytic cell 10.

A second difference is that the device includes a sheath of water-swellable material 42 which, when subjected to the body fluids, expands substantially, as shown in FIG. 7, in order to control the residence time of the device in the subject's body cavity. Sheath 42 is of a material which also dissolves, or is otherwise disintegrated, in the body fluids. An example of a material which can be used for this purpose is ground barley mixed with a starch binder and compressed into a rigid form.

Figure 8:
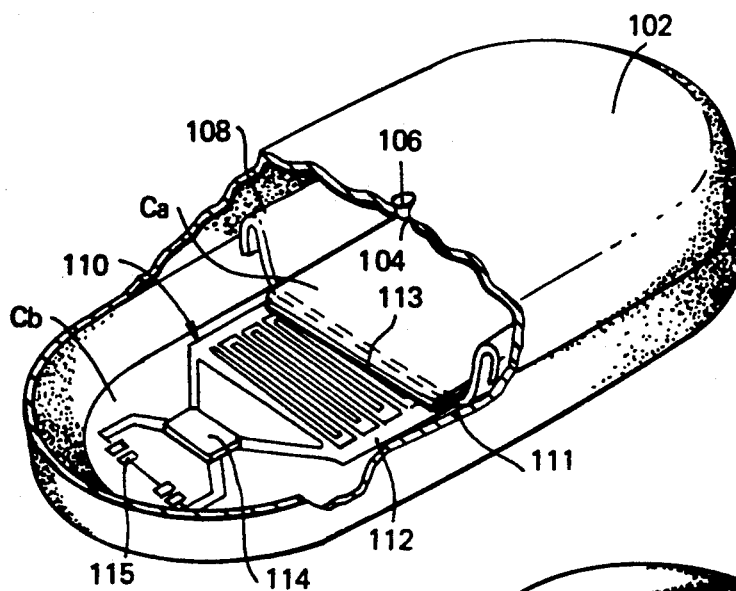
FIG. 8 is a cut-away view of another form of device constructed in accordance with the present invention.

FIG. 8 illustrates another construction, also including a housing 102 of a size enabling it to be swallowed by the subject and of a material which is insoluble in the body cavity (e.g., stomach) fluids. Housing 102 is formed with an opening 104 covered by a plug 106 which is of a material soluble in the body cavity fluids.

Housing 102 further includes a diaphragm 108 dividing the interior of the housing into two expansible-contractible chambers, Ca, Cb. Chamber Ca communicates with housing opening 104 and is adapted to receive the medication to be delivered by the device; and chamber Cb is a control chamber which includes the gas generating means. The latter means is in the form of an electrolytic cell 110 comprising an electrolyte 111 and a pair of electrodes 112, 113 on opposite sides of the electrolyte for supplying electrical current to it. Chamber Cb also includes the microprocessor 114 and electrical circuitry, schematically shown at 115, controlling the microprocessor.

The microprocessor may be preprogrammed to control the time and rate at which electrical current is supplied by the electrodes 112, 113, to the electrolyte 111, and thereby the time and rate of delivery of the medication via outlet 104. It will be appreciated that the device of FIG. 8 could also include one or more of the other features described above, such as the diverse electrodes defining a galvanic cell for energizing the electrolytic cell, the sensors for sensing various conditions within the body, the RF control unit, or the magnetically-actuated or manually-actuated switch for controlling the electrolytic cell externally of the subject.

Figure 9:
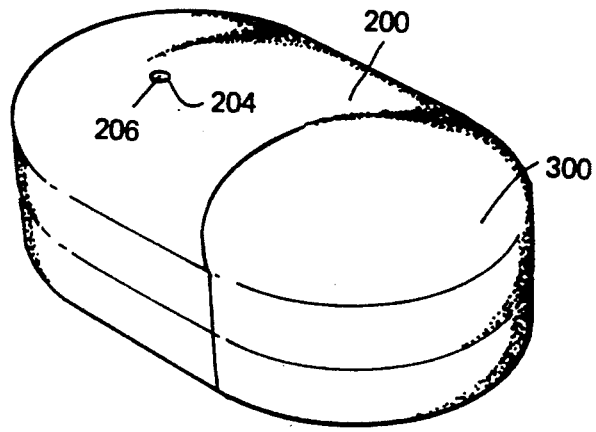
FIGS. 9 and 10 illustrate a further form of device constructed in accordance with the invention, FIG. 9 illustrating the device in its assembled condition, and FIG. 10 illustrating the device before assembly with its two parts being partially cut-away to show internal structure.
Figure 10:
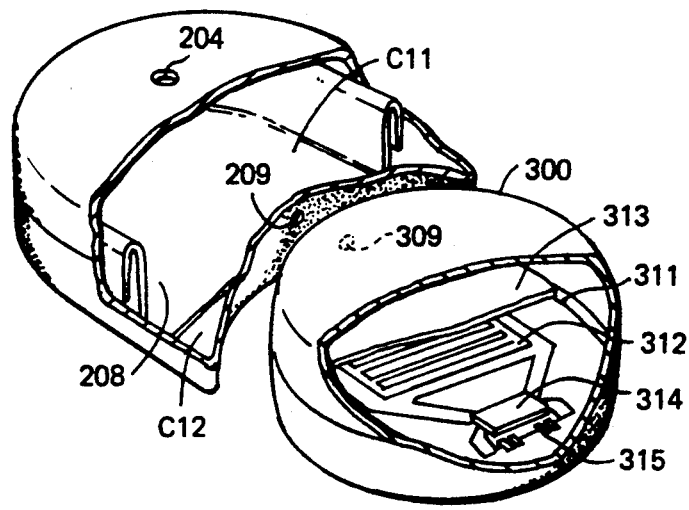

FIGS. 9 and 10 illustrate a further variation wherein the device is constructed of two separate parts or housings 200, 300 joined together before the device is introduced into the body cavity, e.g., before being swallowed by the subject. Housing 200 is of a material which is insoluble in the stomach, but preferably biodegradable in the intestines so that it is not discharged in tact from the subject. Housing 300 is preferably not biodegradable, i.e. insoluble in the stomach and in the intestines. Housing 300 is of circular shape, and housing 200 is formed with a side 202 of concave configuration to accommodate housing 300.

Housing 200 is adapted to receive the medication and is formed with the outlet opening 204 normally covered by the plug 206 made of a material soluble in the stomach fluids. It includes the displaceable diaphragm 208 dividing its interior into the medication chamber $C_{11}$ and the control chamber $C_{12}$.

Housing 300 includes the gas-generating elements. The gas is fed into the control chamber $C_{12}$ via an opening 209 formed in housing 200, and another opening 309 formed in housing 300 when the two housings are fixed together as shown in FIG. 9. The gas is generated by an electrolytic cell 310 comprising an electrolyte 311 and electrodes 312, 313 on its opposite sides. A microprocessor 314 and control circuitry 315 control the time and rate of delivery of electrical current to the electrolytic cell, and thereby the time and rate of delivery of gas via openings 309 and 209 to the control chamber $C_{12}$ in housing 200, and the time and rate of delivery of the medication from chamber $C_{11}$ in housing 200 via the outlet opening 204.

The variation illustrated in FIGS. 9 and 10 may also include the features of any of the other described embodiments.

While the invention has been described with respect to several preferred embodiments, it will be appreciated that many other variations of the invention may be made. Thus, other propelling means could be used, or other gas generating means could be included in chamber $C_2$. For example, there could be used a material which decomposes to generate a gas when subjected to body fluids entering the device via an opening initially covered by a dissolvable plug corresponding to opening 4 and plug 6 with respect to chamber $C_1$. In addition, the diaphragm 8 could be another form of displaceable member, e.g. a piston. Further, the device could be embodied in a capsule or suppository to be taken other than orally, or could be introduced into a body cavity surgically, or could be implanted subcutaneously. Many other variations, modifications and applications of the invention will be apparent.

What is claimed is:

1. A medication administering device, comprising:
   a housing of a size enabling it to be introduced into a body cavity of a subject;
   a displaceable member in the interior of the housing and defining first and second expansible-contractible chambers therein;
   said first chamber including an opening and being adapted to receive medication to be delivered through said opening when said device is in the body cavity;
   gas generating means for supplying a gas to said second chamber to expand it and thereby to force medication from said first chamber out through said opening into the body cavity, said gas generating means including electrically-controlled means for generating a gas when energized;
   and a sensor within said housing for sensing a condition in the body cavity and for controlling said electrically-controlled means in response thereto.

2. The device according to claim 1, wherein said displaceable member is a diaphragm.

3. The device according to claim 1, wherein said opening is initially closed by a material which is soluble in the body cavity fluids.

4. The device according to claim 1, wherein said electrically-controlled means includes an electrolytic cell having an electrolyte generating a gas in accordance with the electrical current passed through the electrolyte.

5. The device according to claim 4, wherein said device further includes a pre-programmable microprocessor for controlling the electrical current to said electrolytic cell and thereby the time and rate at which medication is forced out of said first chamber.

6. The device according to claim 1, wherein said housing further includes a radio frequency receiver for receiving a radio frequency signal for controlling said electrically-controlled means.

7. The device according to claim 1, wherein said housing further includes an electrical switch manually actuatable from externally of the housing for actuating said electrically-controlled means.

8. The device according to claim 1, wherein said electrically-controlled means includes an electrical switch magnetically actuated by a magnetic field externally of the subject.

9. The device according to claim 1, wherein said gas generating means is in said second chamber.

10. The device according to claim 1, wherein said gas generating means is included in a second housing which is attached to the first-mentioned housing when introduced into the body cavity of a subject and which is also of a material insoluble in the body cavity fluids, the two housings being formed with aligned openings for feeding gas generated in said second housing into said second chamber of the first-mentioned housing.

11. A medication administering device, comprising:
 a housing of a size enabling it to be introduced into a body cavity of a subject;
 a displaceable member in the interior of the housing and defining first and second expansible-contractible chambers therein;
 said first chamber including an opening and being adapted to receive medication to be delivered through said opening when said device is in the body cavity;
 and gas generating means for supplying a gas to said second chamber to expand it and thereby to force medication from said first chamber out through said opening into the body cavity, said gas generating means including electrically-controlled means for generating a gas when energized;
 the outer surface of the housing including spaced, diverse metal elements which are bridged by the body cavity fluids to generate an electromotive force for supplying current to the electrically-controlled means.

12. The device according to claim 11, wherein said diverse metal elements are in the form of spaced strips wound on the outer surface of said housing.

13. The device according to claim 11, wherein said housing includes a battery for supplying current to the electrically-controlled means.

14. The device according to claim 11, wherein said housing includes a sensor for sensing a condition in the body cavity and for controlling said electrically-controlled means in response thereto.

15. A medication administering device, comprising:
 a housing of a size enabling it to be introduced into a body cavity of a subject;
 a displaceable member in the interior of the housing and defining first and second expansible-contractible chambers therein;
 said first chamber including an opening and being adapted to receive medication to be delivered through said opening when said device is in the body cavity;
 and gas generating means for supplying a gas to said second chamber to expand it and thereby to force medication from said first chamber out through said opening into the body cavity, said gas generating means including electrically-controlled means for generating a gas when energized;
 said housing including an outer sheath of a liquid-swellable material which swells when in contact with body cavity fluids and disintegrates over a period of time in the body cavity, to thereby control the residence time of the device in the body cavity.

16. A medication administering device, comprising:
 a first housing of a size enabling it to be introduced into a body cavity of a subject, said housing being of a material insoluble in body cavity fluids but being formed with an opening;
 a plug which is soluble in the body cavity fluids closing said opening;
 a displaceable diaphragm in the interior of the housing and defining first and second expansible-contractible chambers therein;
 said first chamber including said opening and being adapted to receive medication to be delivered through said opening when said device is in the body cavity;
 and gas generating means in said second chamber for supplying a gas to said second chamber to expand it and thereby to force medication from said first chamber out through said opening into the body cavity;
 said has generating means in included in a second housing which is attached to said first housing when introduced into the body cavity of a subject and which is also of a material insoluble in the body cavity fluids, the two housing being formed with aligned openings for feeding gas generated in said second housing into said second chamber of the first-mentioned housing.

17. The device according to claim 16, wherein said first housing is bio-degradable, and said second housing is not bio-degradable.

18. The device according to claim 16, wherein said device further includes a pre-programmable microprocessor for controlling the time and rate of gas generating by said gas generating means, and thereby the time and rate at which said medication is forced out of said first chamber.

* * * * *